US009999386B2

(12) United States Patent
Laura Lapoint et al.

(10) Patent No.: US 9,999,386 B2
(45) Date of Patent: Jun. 19, 2018

(54) METHOD AND SYSTEM TO DIAGNOSE CENTRAL SLEEP APNEA

(75) Inventors: Manuel Laura Lapoint, Pittsburgh, PA (US); Sara Marie Sibenaller, Pittsburgh, PA (US); Lauren Elizabeth Hueser, Brighton, MA (US)

(73) Assignee: Koninklijke Philips N.V., Eindhoven (NL)

( * ) Notice: Subject to any disclaimer, the term of this patent is extended or adjusted under 35 U.S.C. 154(b) by 1044 days.

(21) Appl. No.: 14/003,249

(22) PCT Filed: Mar. 12, 2012

(86) PCT No.: PCT/IB2012/051139
§ 371 (c)(1),
(2), (4) Date: Sep. 5, 2013

(87) PCT Pub. No.: WO2012/123878
PCT Pub. Date: Sep. 20, 2012

(65) Prior Publication Data
US 2013/0345589 A1    Dec. 26, 2013

Related U.S. Application Data

(60) Provisional application No. 61/453,253, filed on Mar. 16, 2011.

(51) Int. Cl.
*A61B 5/08*     (2006.01)
*A61B 5/00*     (2006.01)

(52) U.S. Cl.
CPC .......... *A61B 5/4818* (2013.01); *A61B 5/0803* (2013.01)

(58) Field of Classification Search
CPC ....... A61B 5/0803; A61B 5/4818; A61B 5/08; A61B 5/0816; A61B 5/082; A61B 5/0826; A61B 5/087; A61B 5/0873; A61B 5/091
See application file for complete search history.

(56) References Cited

U.S. PATENT DOCUMENTS 4,637,385 A * 1/1987 Rusz .................... A61M 16/00
                                                    128/204.21
4,777,962 A * 10/1988 Watson ................ A61B 5/1135
                                                    600/529

(Continued)

FOREIGN PATENT DOCUMENTS

EP          2245985 A1    11/2010
WO     2008021222 A2      2/2008
(Continued)

OTHER PUBLICATIONS

Gianfranco Parati et al; "Device-Guide Paced Breathing in the Home Setting: Effects on Exercise Capacity, Pulmonary and Ventricular Function in Patients With Chronic Heart Failure: A Pilot", Circulation Heart Failure, Journal of the American Heart Assoication, 2008, vol. 1, pp. 178-1783.

(Continued)

*Primary Examiner* — Navin Natnithithadha

(57) ABSTRACT

Methods and system to diagnose central sleep apnea of a patient employ a relatively short test, combining few breathing parameters. The test is short in comparison to commonly used time-consuming and complex multi-parameter sleep studies. The patient uses a positive airway pressure device, and follows breathing cues. The occurrence of a central apnea during the delivery of breathing cues may support a diagnosis of central sleep apnea.

12 Claims, 2 Drawing Sheets

(56) References Cited

U.S. PATENT DOCUMENTS

Figure 1:
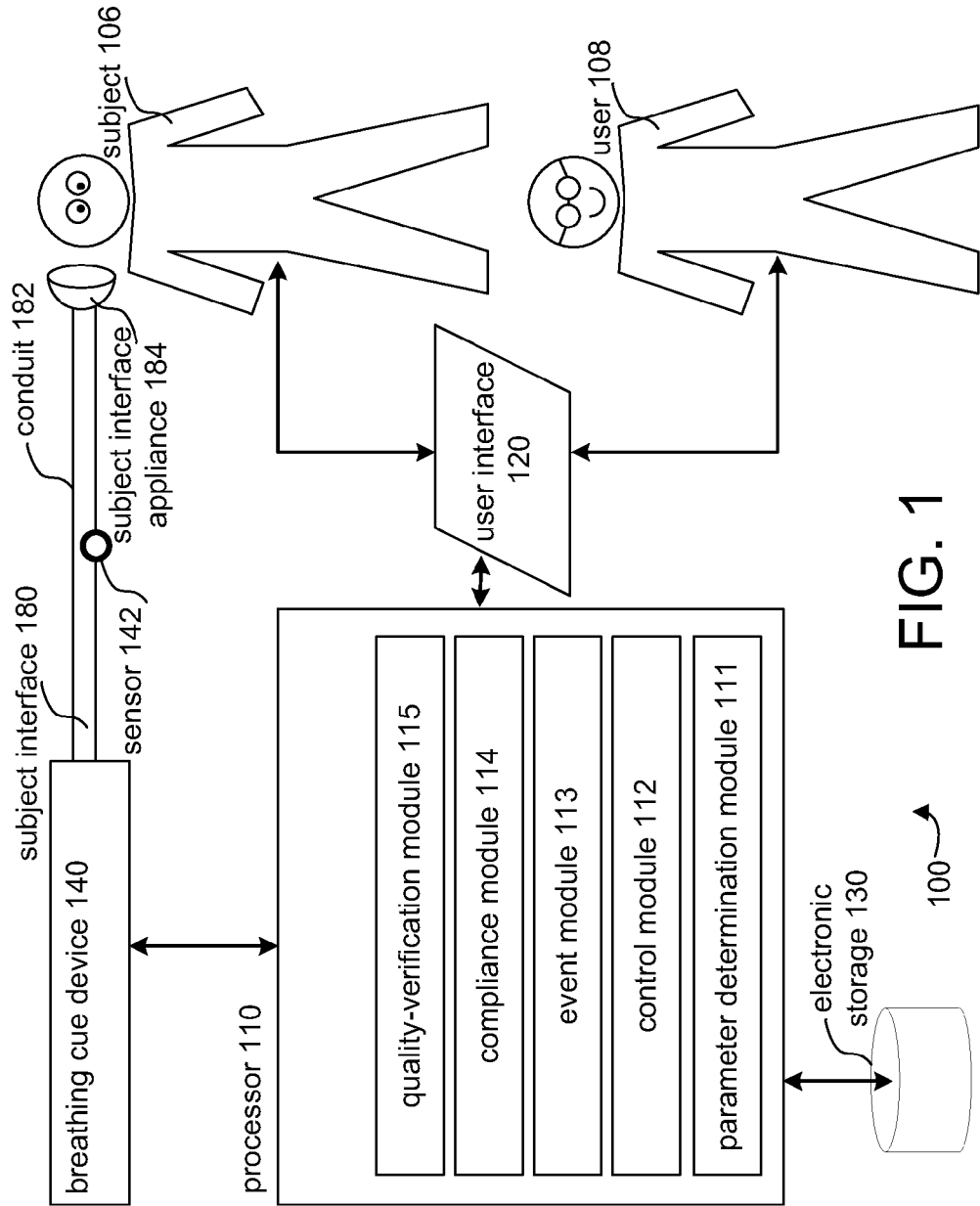

| | | | | |
|---|---|---|---|---|
| 4,860,766 | A * | 8/1989 | Sackner | A61B 5/113 600/534 |
| 5,076,281 | A * | 12/1991 | Gavish | A61B 5/6831 128/905 |
| 5,800,337 | A * | 9/1998 | Gavish | A61B 5/1135 600/27 |
| 6,090,037 | A * | 7/2000 | Gavish | A61B 5/1135 600/27 |
| 6,105,575 | A * | 8/2000 | Estes | A61M 16/00 128/204.21 |
| 6,273,088 | B1 * | 8/2001 | Hillsman | A61M 16/00 128/204.18 |
| 6,609,517 | B1 | 8/2003 | Estes et al. | |
| 6,662,032 | B1 * | 12/2003 | Gavish | A61B 5/1135 600/300 |
| 6,752,151 | B2 * | 6/2004 | Hill | A61M 16/00 128/204.18 |
| 7,168,429 | B2 * | 1/2007 | Matthews | A61M 16/0051 128/204.21 |
| 7,267,122 | B2 * | 9/2007 | Hill | A61M 16/00 128/204.18 |
| 7,556,038 | B2 | 7/2009 | Kirby et al. | |
| 7,690,378 | B1 * | 4/2010 | Turcott | A61B 5/0816 128/201.23 |
| 7,810,497 | B2 * | 10/2010 | Pittman | A61M 16/0069 128/204.18 |
| 7,827,988 | B2 * | 11/2010 | Matthews | A61M 16/0051 128/204.21 |
| 7,850,619 | B2 * | 12/2010 | Gavish | A61B 7/003 600/484 |
| 7,938,114 | B2 * | 5/2011 | Matthews | A61M 16/0051 128/204.18 |
| 8,136,521 | B2 * | 3/2012 | Matthews | A61M 16/0051 128/200.24 |
| 8,140,164 | B2 * | 3/2012 | Tehrani | A61N 1/3601 607/42 |
| 8,545,416 | B1 * | 10/2013 | Kayyali | A61B 5/085 128/204.23 |
| 9,295,797 | B2 * | 3/2016 | Shissler | A61B 5/0826 |
| 9,629,970 | B2 * | 4/2017 | Matthews | A61M 16/0051 |
| 2003/0111079 | A1 * | 6/2003 | Matthews | A61M 16/0051 128/204.18 |
| 2004/0116784 | A1 * | 6/2004 | Gavish | A61B 5/0205 600/300 |
| 2004/0138576 | A1 | 7/2004 | Wright et al. | |
| 2004/0187870 | A1 * | 9/2004 | Matthews | A61M 16/0051 128/204.22 |
| 2006/0000475 | A1 * | 1/2006 | Matthews | A61M 16/0051 128/204.21 |
| 2007/0221224 | A1 * | 9/2007 | Pittman | A61M 16/0069 128/204.22 |
| 2008/0035147 | A1 | 2/2008 | Kirby et al. | |
| 2008/0041382 | A1 * | 2/2008 | Matthews | A61M 16/0051 128/204.23 |
| 2008/0041383 | A1 * | 2/2008 | Matthews | A61M 16/0051 128/204.23 |
| 2008/0161878 | A1 * | 7/2008 | Tehrani | A61N 1/3601 607/42 |
| 2008/0319333 | A1 * | 12/2008 | Gavish | A61B 7/003 600/529 |
| 2009/0025725 | A1 | 1/2009 | Remmers | |
| 2010/0252037 | A1 | 10/2010 | Wondka et al. | |
| 2012/0152252 | A1 * | 6/2012 | Matthews | A61M 16/0051 128/204.23 |
| 2013/0197601 | A1 * | 8/2013 | Tehrani | A61N 1/3601 607/42 |

FOREIGN PATENT DOCUMENTS

| | | |
|---|---|---|
| WO | 2010106451 A1 | 9/2010 |
| WO | 2010116276 A1 | 10/2010 |

OTHER PUBLICATIONS

Holger Steltner et al; "Diagnosis of Sleep Apnea by Automatic Analysis of Nasal Pressure and Forced Oscillation Impedance", American Journal CRLT Care Med, vol. 165, No. 7, pp. 940-944, 2002.

Robert Josehp Thomoas et al; "Differentiating Obstructive From Central and Complex Sleep Apnea Using an Automated Electrocardiogram-Based Method", Sleep, vol. 30, No. 12, Dec. 1, 2007, pp. 1756-1769.

"View a Sleep Study", Talk About Sleep, pp. 1-5, 2010.

* cited by examiner

METHOD AND SYSTEM TO DIAGNOSE CENTRAL SLEEP APNEA

FIELD

The present disclosure pertains to a method and apparatus for diagnosing central sleep apnea for a patient, and, in particular, avoiding a complex and time-consuming polysomnogram to make such a diagnosis.

DESCRIPTION OF THE RELATED ART

It is well known to diagnose central sleep apnea and similar breathing disorders by using a polysomnogram or sleep study. A polysomnogram is a complex, costly, and time-consuming multi-parameter test. A patient, or subject, is required to spend an entire night connected to a variety of sensors. There is a need for improved methods and systems to support a diagnosis of central sleep apnea.

Accordingly, it is an object of one or more embodiments of the present invention to provide a system configured to support diagnosis of central sleep apnea of a subject using a test. The system comprises a device configured to deliver breathing cues to a self-ventilating subject, one or more sensors that generate output signals conveying information related to parameters associated with the gas, and one or more executable computer program modules. The breathing cues prompt the self-ventilating subject to breathe a gas and/or consciously alter one or more breathing parameters. The computer program modules may include a parameter determination module, a control module, and an event module. The parameter determination module is configured to determine a first and a second breathing parameter from the output signals generated by the sensors. The control module is configured to control the device to regulate the breathing cues to adjust the first and/or second breathing parameter. The event module is configured to detect an occurrence of a central apnea based on the first and/or second breathing parameter during delivery of breathing cues.

It is yet another aspect of one or more embodiments of the present invention to provide a method of diagnosing central sleep apnea of a subject during a test. The method comprises delivering breathing cues that prompt a self-ventilating subject to breathe a gas, generating output signals conveying information related to parameters associated with the gas, determining a first and second breathing parameters from the generated output signals, regulating the breathing cues to adjust the first and/or second breathing parameter, and detecting an occurrence of a central apnea based on the first and/or second breathing parameter during delivery of breathing cues.

It is yet another aspect of one or more embodiments to provide a system configured to diagnose central sleep apnea of a subject during a test. The system comprises a means for delivering breathing cues to a self-ventilating subject that prompt the self-ventilating subject to breathe a gas, a means for generating one or more output signals conveying information related to one or more parameters associated with the gas, a means for determining a first breathing parameter and a second breathing parameter from the one or more generated output signals, a means for regulating the breathing cues to adjust the first and/or second breathing parameter, and a means for detecting an occurrence of a central apnea based on the first and/or second breathing parameter during delivery of breathing cues.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

Figure 2:
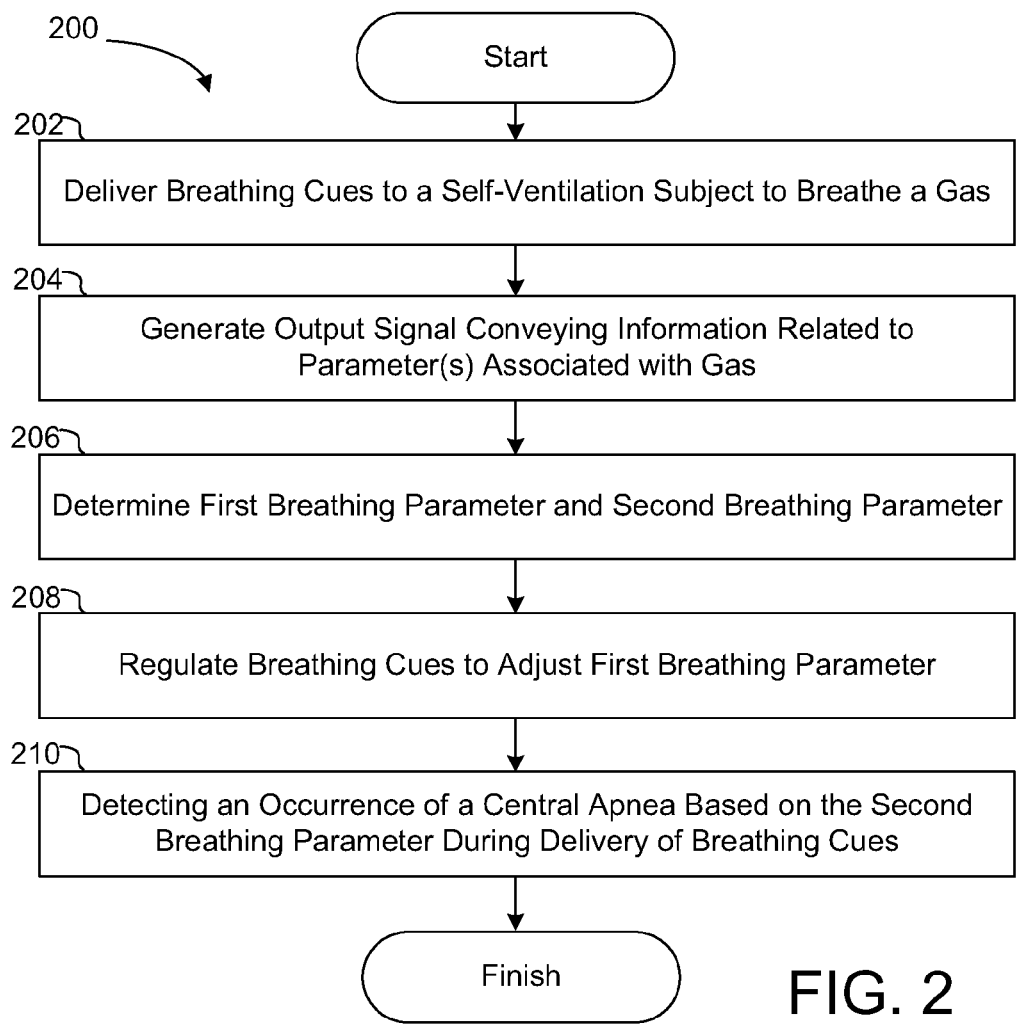

FIG. 1 schematically illustrates a system configured to support diagnosis of central sleep apnea of a subject using a test; and FIG. 2 illustrates a method for diagnosing central sleep apnea of a subject during a test.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Using a polysomnogram is a common way to diagnose central sleep apnea and similar breathing disorders in a patient, or "subject". The usage of polysomnograms is maligned for multiple reasons, including test complexity, test duration, patient discomfort, costs, and/or other reasons. Central sleep apnea (or central sleep apnea syndrome) is a collective term referring to breathing disorders including Cheyne-Stokes respiration, periodic breathing, and/or other breathing disorders.

FIG. 1 schematically illustrates a system 100 configured to support diagnosis of central sleep apnea of a subject using a test. In particular, system 100 delivers breathing cues to a subject 106, monitors how well subject 106 follows the breathing cues during the comparatively short test detects any occurrence of central apneas during the test based on one or more breathing parameters, and supports a diagnosis of central sleep apnea by analyzing the monitored and detected information. The duration of the test is short compared to a full-night polysomnogram or sleep study, which can take eight hours or more. In one embodiment, system 100 comprises one or more of a processor 110, a breathing cue device 140, a sensor 142, an electronic storage 130, a user interface 120, a subject interface 180, and/or other components.

Breathing cue device 140 may be integrated, combined, or connected with a pressure generator or positive airway pressure (PAP) device configured to provide a pressurized flow of breathable gas to the airway of subject 106, e.g. via subject interface 180. Subject 106 may be self-ventilating and referred to as such throughout this specification. Self-ventilating, as used herein, refers to a subject initiating his or her own inspiration and/or expiration, regardless of pressure support or the occurrence of breathing cues. Breathing cue device 140 is configured to deliver breathing cues to subject 106 that prompt subject 106 to take respiratory action (e.g., begin an inhalation, begin an exhalation, and/or take other respiratory action). An example of a method implementing the stated function attributed to breathing cue device 140 is disclosed (as "paced breathing (PB) method") in U.S. patent application Ser. No. 11/836,292, filed Aug. 9, 2007, which is hereby incorporated by reference herein in its entirety.

In some embodiments, breathing cues prompting a subject to breathe in or out are implemented as a higher and lower positive pressure of a (multi-level) PAP device, respectively. For example, to prompt subject 106 to inhale, the pressure of the pressurized flow of breathable gas may be increased to an Inspiratory Positive Air Pressure (IPAP). Similarly, to prompt subject 106 to exhale, the pressure of the pressurized flow of breathable gas may be decreased to an Expiratory Positive Air Pressure (EPAP). Other schemes for providing breathing cues through the delivery of the pressurized flow of breathable gas are contemplated. A PAP device may be configured such that one or more gas parameters of the pressurized flow of breathable gas are controlled in accordance with a therapeutic respiratory regimen for subject 106. The one or more gas parameters may include, for example, one or more of flow, pressure, humidity, velocity, acceleration, and/or other parameters. In one embodiment, breathing cue device 140 is part of a positive airway pressure device configured to provide types of therapy other than ventilation, including types of therapy where a subject performs expiration of his own accord or where the device provides negative pressure.

In certain embodiments, breathing cues may be sensory indications that one or more respiratory actions should be taken, that one or more events have occurred (or will occur), and/or indicating other information. Breathing cues may include one or more of an auditory indication, a visual indication, a tactile indication, and/or other indications. Indications may include a sequence of multiple auditory indications, visual indications, tactile indications, and/or other indications. An auditory indication may be an audible sound. A visual indication may be a flashing light. A tactile indication may be a vibration.

A pressurized flow of breathable gas may be delivered from breathing cue device 140 to the airway of subject 106 by a subject interface 180. Subject interface 180 may include a conduit 182 and/or a subject interface appliance 184. Conduit 182 may be a flexible length of hose, or other conduit, that places subject interface appliance 184 in fluid communication with breathing cue device 140. Conduit 182 forms a flow path through which the pressurized flow of breathable gas is communicated between subject interface appliance 184 and breathing cue device 140.

Subject interface appliance 184 may be configured to deliver the pressurized flow of breathable gas to the airway of subject 106. As such, subject interface appliance 184 may include any appliance suitable for this function. In one embodiment, breathing cue device 140 is a dedicated ventilation device and subject interface appliance 184 is configured to be removably coupled with another interface appliance being used to deliver respiratory therapy to subject 106. For example, subject interface appliance 184 may be configured to engage with and/or be inserted into an endotracheal tube, a tracheotomy portal, and/or other interface appliances. In one embodiment, subject interface appliance 184 is configured to engage the airway of subject 106 without an intervening appliance. In this embodiment, subject interface appliance 184 may include one or more of an endotracheal tube, a nasal cannula, a tracheotomy tube, a nasal mask, a nasal/oral mask, a full face mask, a total face mask, a partial rebreathing mask, or other interface appliances that communicate a flow of gas with an airway of a subject. The present disclosure is not limited to these examples, and contemplates delivery of the pressurized flow of breathable gas to subject 106 using any subject interface.

System 100 may include electronic storage 130 comprising electronic storage media that electronically stores information. The electronic storage media of electronic storage 130 may include one or both of system storage that is provided integrally (i.e., substantially non-removable) with system 100 and/or removable storage that is removably connectable to system 100 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 100 to function properly. For example, electronic storage 130 may record or store one or more parameters (as discussed elsewhere herein), information indicating whether the self-ventilating subject adequately complied with the delivered breathing cues during the test, information indicating whether a central apnea occurred, and/or other information. Electronic storage 130 may be a separate component within system 100, or electronic storage 130 may be provided integrally with one or more other components of system 100 (e.g., processor 110).

System 100 may include user interface 120 configured to provide an interface between system 100 and a user (e.g., user 108, subject 106, a caregiver, a therapy decision-maker, etc.) through which the user can provide information to and receive information from system 100. This enables data, results, and/or instructions and any other communicable items, collectively referred to as "information," to be communicated between the user and system 100. An example of information that may be conveyed to subject 106 is a breathing cue or an indication related to a breathing cue that substantially coincides with a breathing cue. Information related to a breathing cue may include, for example, an instruction to begin exhaling, to end exhaling, to begin inhaling, to end inhaling, to breathe faster, to breathe slower, to increase flow, to decrease flow, to pause respiration, and/or to otherwise consciously alter one or more breathing parameters. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information related to the breathing cues may e.g. be provided to subject 106 by user interface 120 in the form of auditory signals, visual signals, tactile signals, and/or other sensory signals.

By way of non-limiting example, user interface 120 may include a radiation source capable of emitting light. The radiation source may include, for example, one or more of at least one LED, at least one light bulb, a display screen, and/or other sources. User interface 120 may control the radiation source to emit light in a manner that conveys to subject 106 information related to the breathing cues being provided to subject 106 by the pressurized flow of breathable gas. For instance, the radiation source may emit light when the breathing cues are prompting subject 106 to inhale, and may stop emitting light, or emit light of a different color, when the breathing cues are prompting subject 106 to exhale. The intensity of the light emitted by the radiation source may convey to subject 106 the magnitude of the flow that the breathing cues are prompting subject 106 to generate during respiration. Note that the subject and the user of system 100 may be one and the same person.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 100 from removable storage (e.g., a smart card, a flash drive, a removable disk, etc.) that enables the user(s) to customize the implementation of system 100. Other exemplary input devices and techniques adapted for use with system 100 as user interface 120 include, but are not limited to, an RS-232 port, RF link, an IR link, modem (telephone, cable, Ethernet, internet or other). In short, any technique for communicating information with system 100 is contemplated as user interface 120.

Sensor 142 is configured to generate one or more output signals conveying measurements related to respiratory parameters, including one or more of flow, pressure, humidity, velocity, acceleration, and/or other respiratory parameters. Output signals may convey measurements related to parameters of thoracic respiratory effort, abdominal respiratory effort, and/or other respiratory effort parameters. Based on these respiratory parameter and/or respiratory effort parameters, parameter determination module 111 (and/or other components of system 100) may be configured to determine one or more breathing parameters, including (tidal) volume, respiratory rate, breathing period, inhalation time or period, exhalation time or period, peak flow, flow rate, respiration flow curve shape, transition time from inhalation to exhalation and/or vice versa, transition time from peak inhalation flow rate to peak exhalation flow rate and/or vice versa, respiration pressure curve shape, and/or other breathing parameters. For example, a thoracic respiratory effort sensor may be operatively connected to the chest of the subject, and comprise a so-called effort belt. Alternatively, and/or simultaneously, an abdominal respiratory effort sensor may be operatively connected to the abdomen of the subject, and comprise an effort belt. Sensor 142 may be in fluid communication with conduit 182 and/or subject interface appliance 184.

The illustration of sensor 142 as including a single member in FIG. 1 is not intended to be limiting. In one embodiment sensor 142 includes a plurality of sensors operating as described above by generating output signals conveying information related to parameters associated with the gas breathed by subject 106, the delivery of the gas to subject 106, and/or a respiratory effort by the subject. For example, a breathing parameter may be related to a mechanical unit of measurement of a component of breathing cue device 140 (or of a device that breathing cue device 140 is integrated, combined, or connected with) such as rotor speed, motor speed, blower speed, fan speed, or a related measurement that may serve as a proxy for any of the previously listed breathing parameters through a previously known/calibrated mathematical relationship. Resulting signals or information from sensor 142 may be transmitted to processor 110, user interface 120, and/or electronic storage 130. This transmission can be wired and/or wireless.

Processor 110 is configured to provide information processing capabilities in system 100. As such, processor 110 includes one or more of a digital processor, an analog processor, a digital circuit designed to process information, an analog circuit designed to process information, a state machine, and/or other mechanisms for electronically processing information. Although processor 110 is shown in FIG. 1 as a single entity, this is for illustrative purposes only. In some implementations, processor 110 includes a plurality of processing units.

As is shown in FIG. 1, processor 110 is configured to execute one or more computer program modules. The one or more computer program modules include one or more of a parameter determination module 111, a control module 112, an event module 113, a compliance module 114, a quality-verification module 115, and/or other modules. Processor 110 may be configured to execute modules 111, 112, 113, 114, and/or 115 by software; hardware; firmware; some combination of software, hardware, and/or firmware; and/or other mechanisms for configuring processing capabilities on processor 110.

It should be appreciated that although modules 111, 112, 113, 114, and 115 are illustrated in FIG. 1 as being co-located within a single processing unit, in implementations in which processor 110 includes multiple processing units, one or more of modules 111, 112, 113, 114, and/or 115 may be located remotely from the other modules. The description of the functionality provided by the different modules 111, 112, 113, 114, and/or 115 described below is for illustrative purposes, and is not intended to be limiting, as any of modules 111, 112, 113, 114, and/or 115 may provide more or less functionality than is described. For example, one or more of modules 111, 112, 113, 114, and/or 115 may be eliminated, and some or all of its functionality may be provided by other ones of modules 111, 112, 113, 114, and/or 115. Note that processor 110 may be configured to execute one or more additional modules that may perform some or all of the functionality attributed below to one of modules 111, 112, 113, 114, and/or 115.

Parameter determination module 111 is configured to determine one or more breathing parameters from the output signals generated by sensor 142. The one or more breathing parameters may include a first breathing parameter, a second breathing parameter, and/or other parameters. A breathing parameter may include a respiratory parameter derived from one or more gas parameters of the pressurized flow of breathable gas. Such (gas) parameters may include one or more of a tidal volume of the breathing of the self-ventilating subject, a respiratory rate, an inhalation time, an exhalation time, a flow rate of the breathing of the self-ventilating subject, and/or other breathing parameters. Breathing parameters may be related to and/or derived from measurements of one or more of (peak) flow, pressure, temperature, humidity, velocity, acceleration, gas composition (e.g. concentration(s) of one or more constituents), thermal energy dissipated, and/or other gas parameters of the pressurized flow of breathable gas. Breathing parameters may be associated with specific timing within a breathing cycle or within the duration of the test. For example, end pressure may be measured at the end of an expiration when the flow at of near the airway of the subject is minimized. Additionally, breathing parameters may indicate respiratory effort of subject 106. This may include one or more of a thoracic respiratory effort, an abdominal respiratory effort of the self-ventilating subject, and/or other parameters indicating respiratory effort. In certain embodiments a breathing parameter may be related to and/or derived from a similar measurement as used to generate another breathing parameter, though using a different specific timing within a breathing cycle or within the duration of the test. For example, the first breathing parameter and the second breathing parameter could both be a duration of exhalation. As another example, the first breathing parameter and the second breathing parameter could both indicate thoracic respiratory effort.

Control module 112 is configured to control breathing cue device 140 in the provision of breathing cues to subject 106. As such, control module 112 may control the timing, the type, the magnitude, and/or other aspects of the breathing cues in accordance with a therapy regime to adjust one or more parameters of the respiration of subject 106. Such parameters may include a first breathing parameter determined by parameter determination module 111. The determination of the first breathing parameter may be used by control module 112 in a feedback manner in determining the breathing cues that should be provided to subject 106. For example, by increasing the rate of the breathing cues, the respiratory rate of subject 106 is increased. As another example, by increasing the rate of the breathing cues, the rate of signals indicating thoracic respiratory effort is increased.

In implementations in which the breathing cues include the elevation of pressure to IPAP to prompt inhalation, and the lowering of EPAP to prompt exhalation, control module 112 may determine the appropriate levels of IPAP and EPAP. This determination may be based on one or more user configurable settings, based on measurements taken during spontaneous respiration by subject 106, responsiveness of subject 106 to the breathing cues, and/or other parameters. Control module 112 may be configured to adjust the pressure difference between IPAP and EPAP (e.g., on one or more of the basis described herein). Pressure differences may be less than 3 cm-$H_2O$, less than 4 cm-$H_2O$, less than 5 cm-$H_2O$, less than 6 cm-$H_2O$, more than 1 cm-$H_2O$, more than 2 cm-$H_2O$, between 2 and 6 cm-$H_2O$, between 1 and 5 cm-$H_2O$, and/or other pressure difference minimums, pressure difference maximums, or ranges of pressure differences. It will be appreciated that the unit of pressure used herein is not limited to cm-$H_2O$, which is commonly used in relation to the operation of PAP devices.

Event module 113 is configured to detect an occurrence of a central apnea based on a breathing parameter—determined by parameter determination module 111—during delivery of breathing cues by breathing cue device 140. For example, event module 113 can detect a lack (or significantly reduced level) of respiratory effort (e.g., thoracic respiratory effort and/or abdominal respiratory effort). The lack of effort may be accompanied by a significant reduction in tidal volume (and/or other breathing parameters). As another example, event module 113 can detect if cessation of breathing has occurred by monitoring, measuring, and/or analyzing tidal volume, duration of exhalation, and/or other (gas) parameters. Such a detection may indicate the occurrence of a central apnea during the test. The occurrence of a central apnea during a test duration is a prerequisite for a diagnosis of central sleep apnea.

Compliance module 114 is configured to determine whether the self-ventilating subject adequately complies with the breathing cue delivered by breathing cue device 140. For example, compliance module 114 may compare (the timing of) breathing cues by breathing cue device 140 with measurements of a respiratory timing (e.g., inhalation start, exhalation start, respiratory rate, and/or other parameters indicating respiratory timing), to determine whether subject 106, at least for a part of the test, follows the breathing cues properly. It will be appreciated that subject 106 does not follow breathing cues during the occurrence of a central apnea, compliance module 114 is configured to detect instances in which subject 106 is breathing spontaneously, but not following the breathing cues. Compliance with the breathing cues is a prerequisite for a diagnosis of central sleep apnea.

Quality-verification module 115 is configured to verify whether the test was conducted in compliance with a set of quality guidelines. The set of quality guidelines may include a minimum duration of the test, a proper (supine) positioning of subject 106 during the test, a leakage level of the delivery of gas within a predetermined level of acceptable leakage, a difference between higher and lower levels of pressure within a predetermined level of acceptable difference for a test of the nature described herein, and/or other quality guidelines. The test duration may be ten minutes, fifteen minutes, twenty minutes, more than 20 minutes, and/or other time durations. Any test duration shorter than eight hours is short compared to a full-night polysomnogram or sleep study. The methods disclosed herein may be conducted when the subject is awake (during wakefulness), at sleep onset, during sleep, or during a combination of the previous states.

FIG. 2 illustrates a method 200 for diagnosing central sleep apnea of a subject during a test. The operations of method 200 presented below are intended to be illustrative. In some embodiments, method 200 may be accomplished with one or more additional operations not described, and/or without one or more of the operations discussed. Additionally, the order in which the operations of method 200 are illustrated in FIG. 2 and described below is not intended to be limiting.

In some embodiments, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

At an operation 202, breathing cues are delivered to a self-ventilating subject that prompt the self-ventilating subject to breathe a gas. In one embodiment, operation 202 is performed by a breathing cue device similar to or substantially the same as breathing cue device 140 (shown in FIG. 1 and described above).

At an operation 204, one or more output signals conveying information related to one or more parameters associated with the gas are generated. In one embodiment, operation 204 is performed by one or more sensors similar to or substantially the same as sensor 142 (shown in FIG. 1 and described above).

At an operation 206, a first breathing parameter and a second breathing parameter are determined from the one or more generated output signals. In one embodiment, operation 206 is performed by a parameter determination module similar to or substantially the same as parameter determination module 111 (shown in FIG. 1 and described above), operating in conjunction with one or more sensors similar to or substantially the same as sensor 142 (shown in FIG. 1 and described above).

At an operation 208, the breathing cues are regulated to adjust the first breathing parameter. In one embodiment, operation 208 is performed by a control module similar to or substantially the same as control module 112 (shown in FIG. 1 and described above), operating in conjunction with a parameter determination module similar to or substantially the same as parameter determination module 111 (shown in FIG. 1 and described above).

At an operation 210, an occurrence of a central apnea is detected during delivery of breathing cues to a self-ventilating subject, based on the second breathing parameter. In one embodiment, operation 210 is performed by an event module similar to or substantially the same as event module 113 (shown in FIG. 1 and described above), operating in conjunction with a parameter determination module similar to or substantially the same as parameter determination module 111 (shown in FIG. 1 and described above). For example, method 200 may be used to diagnose central sleep apnea of a self-ventilating subject during a test of relatively short duration by combining a first breathing parameter, a second breathing parameter, the information whether the self-ventilating subject adequately complied with the delivered breathing cues during the test, the information whether a central apnea occurred, and/or other information.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A system configured to support diagnosis of central sleep apnea of a subject using a test, the system comprising:
   a device configured to deliver breathing cues by altering a pressure of a pressurized flow of breathable gas to a self-ventilating subject that prompt the self-ventilating subject to breathe the breathable gas;
   one or more sensors that generate one or more output signals conveying information related to one or more parameters associated with the breathable gas; and
   one or more processors configured by machine-readable instructions to:
      determine a first breathing parameter and a second breathing parameter from the one or more output signals generated by the one or more sensors;
      control the device to regulate the breathing cues provided to the self-ventilating subject to adjust the first breathing parameter;
      detect an occurrence of a central apnea based on the second breathing parameter during delivery of breathing cues; and
      verify whether the test was conducted in compliance with a set of quality guidelines, the set of quality guidelines including one or more of a minimum duration of the test; a proper positioning of subject during the test; a leakage level of the delivery of the breathable gas being within a predetermined level of leakage; or a difference between higher and lower levels of pressure being within a predetermined level of difference for the test.

2. The system of claim 1, wherein the one or more processors are further configured to determine whether the self-ventilating subject adequately complies with the delivered breathing cues.

3. The system of claim 1, wherein the one or more output signals convey information related to one or more of a tidal volume of the breathing of the self-ventilating subject, a respiratory rate, an inhalation time, an exhalation time, or a flow rate of the breathing of the self-ventilating subject.

4. The system of claim 1, wherein the one or more output signals convey information related to one or both of a thoracic respiratory effort of the self-ventilating subject and/or an abdominal respiratory effort of the self-ventilating subject.

5. A method of diagnosing central sleep apnea of a subject during a test, the method comprising:
   delivering, using a device, breathing cues by altering a pressure of a pressurized flow of breathable gas to a self-ventilating subject that prompt the self-ventilating subject to breathe the breathable gas;
   generating, using one or more sensors, one or more output signals conveying information related to one or more parameters associated with the breathable gas;
   determining, using one or more processors, a first breathing parameter and a second breathing parameter from the one or more generated output signals;
   controlling, using the one or more processors, the device to regulate the breathing cues to adjust the first breathing parameter;
   detecting, using the one or more processors, an occurrence of a central apnea based on the second breathing parameter during delivery of breathing cues, and
   verifying, using the one or more processors, whether the test was conducted in compliance with a set of quality guidelines, the set of quality guidelines including one or more of a minimum duration of the test, a proper positioning of subject during the test, a leakage level of the delivery of the breathable gas being within a predetermined level of leakage, or a difference between higher and lower levels of pressure being within a predetermined level of difference for the test.

6. The method of claim 5, further comprising determining whether the self-ventilating subject adequately complies with the delivered breathing cues.

7. The method of claim 5, wherein the one or more output signals convey information related to one or both of a thoracic respiratory effort of the self-ventilating subject and/or an abdominal respiratory effort of the self-ventilating subject.

8. The method of claim 5, wherein the one or more output signals convey information related to one or more of a tidal volume of the breathing of the self-ventilating subject, a respiratory rate, an inhalation time, an exhalation time, or a flow rate of the breathing of the self-ventilating subject.

9. A system configured to diagnose central sleep apnea of a subject during a test, the method comprising:

means for delivering breathing cues by altering a pressure of a pressurized flow of breathable gas to a self-ventilating subject that prompt the self-ventilating subject to breathe the breathable gas;

means for generating one or more output signals conveying information related to one or more parameters associated with the breathable gas;

means for determining a first breathing parameter and a second breathing parameter from the one or more generated output signals;

means for regulating the breathing cues to adjust the first breathing parameter;

means for detecting an occurrence of a central apnea based on the second breathing parameter during delivery of breathing cues; and means for verifying whether the test was conducted in compliance with a set of quality guidelines, the set of quality guidelines including one or more of a minimum duration of the test; a proper positioning of subject during the test; a leakage level of the delivery of the breathable gas being within a predetermined level of leakage; or a difference between higher and lower levels of pressure being within a predetermined level of difference for the test.

10. The system of claim 9, further comprising means for determining whether the self-ventilating subject adequately complies with the delivered breathing cues.

11. The system of claim 9, wherein the one or more output signals convey information related to one or more of a tidal volume of the breathing of the self-ventilating subject, a respiratory rate, an inhalation time, an exhalation time, or a flow rate of the breathing of the self-ventilating subject.

12. The system of claim 9, wherein the one or more output signals convey information related to one or both of a thoracic respiratory effort of the self-ventilating subject and/or an abdominal respiratory effort of the self-ventilating subject.

* * * * *